United States Patent [19]

Howard et al.

[11] 4,325,255
[45] Apr. 20, 1982

[54] ULTRASONIC APPARATUS AND METHOD FOR MEASURING THE CHARACTERISTICS OF MATERIALS

[75] Inventors: Paul L. Howard; William B. Tarpley, Jr., both of West Chester; George R. Moulder, Coatesville; William R. McBride, Glenmore, all of Pa.

[73] Assignee: Energy and Minerals Research Co., Exton, Pa.

[21] Appl. No.: 137,879

[22] Filed: Apr. 7, 1980

[51] Int. Cl.³ .................... G01N 29/00; G01F 23/28
[52] U.S. Cl. .................... 73/589; 73/290 V
[58] Field of Search .................... 73/590, 589, 290 V; 340/621

[56] References Cited

U.S. PATENT DOCUMENTS

| 1,990,543 | 2/1935 | Gilson . | |
|---|---|---|---|
| 2,891,180 | 6/1959 | Elmore . | |
| 3,229,523 | 1/1966 | Boyd | 73/290 V |
| 3,246,516 | 4/1966 | Maropis | 73/290 V |
| 3,381,525 | 5/1968 | Kartluke et al. | 73/590 |

*Primary Examiner*—Anthony V. Ciarlante
*Attorney, Agent, or Firm*—Seidel, Gonda, Goldhammer and Panitch

[57] ABSTRACT

Ultrasonic apparatus and method measures the characteristics of materials by sensing changes in the impedance to applied drive excitation of an ultrasonic probe using a crystal sensor that is integral with the ultrasonic transducer.

10 Claims, 4 Drawing Figures

ULTRASONIC APPARATUS AND METHOD FOR MEASURING THE CHARACTERISTICS OF MATERIALS

This invention relates to an ultrasonic apparatus and method for measurement of the characteristics of a material. More particularly, this invention relates to the measurement of the characteristics of a material by determining changes reflected in the ultrasonic impedance of the material in a container or flowing through a container. Examples of the characteristics which can be determined include the density of the material, the level of the material in the container, the position of the interface between materials of different densities, material hardness, particle size and changes in chemical composition which are manifested by changes in a physical/chemical characteristic such as density. With respect to changes in a physical/chemical characteristic, the invention can be used to monitor the curing of resins, concrete and similar materials. Such characteristics can be monitored because they all result in changes in impedance to the delivery of ultrasonic energy into the material through an ultrasonic probe.

The fact that such characteristics can be measured by determining changes in ultrasonic impedance is known. See, for example, U.S. Pat. No. 3,246,516 which discloses an apparatus using ultrasonic energy to determine the interface level of stratified substances, such as liquid, foam or gas. U.S. Pat. No. 3,229,523 discloses an ultrasonic probe for measuring the displacement of the surface level of a liquid by determining reflected power based upon a measurement of the standing wave ratio. U.S. Pat. No. 1,990,543 senses the presence or absence of a material within a container by sensing changes in impedance to the ultrasonic energy coupled into the system.

The present invention is directed to an improvement in ultrasonic apparatus for determining the characteristics of a material by measuring reflected ultrasonic impedance as a function of changes in applied drive excitation of an ultrasonic probe. Although the invention can be used for sensing a wide range of material characteristics, it is principally intended for the density of materials and for use in level detection, particularly in containers or vessels which are difficult to access, such as vessels containing corrosive materials.

Among the advantages of using the apparatus of the present invention is that the probe for delivering the ultrasonic energy into the vessel is self-cleaning; the apparatus is fail safe in operation since even a corroded probe will continue to function until complete failure, and that occurrence can be sensed by the electronics associated with the system; the entire apparatus may be arranged to allow the transducer and electronics to be located remotely and coupled acoustically to the probe in the material to be tested; and the probe may be excited periodically, to inhibit the build up of corrosion products. Still further, the sensed failure of the probe can be indicated by an audio and/or visual alarm.

In accordance with the present invention, the apparatus for sensing changes in reflected ultrasonic impedance uses a crystal sensor which is in series mechanically with and thus in integral with the ultrasonic transducer. As used herein, the word crystal is to be given a broad scope so as to include devices whose electrical output varies with dimensional changes and whose dimensions vary with an applied electrical signal, and includes ceramic, magnetostrictive, piezo-electric, etc. This has the advantage of eliminating the need for inferring impedance by separately measuring the standing wave ratio while at the same time accurately measuring the power delivered to the transducer. Applied power is, of course, directly related to impedance. Stated otherwise, the invention provides a method for directly measuring impedance rather than relying upon an indirect method such as the measurement of the standing wave ratio which is affected by variations in the location of the node and anti-node. Another advantage of measuring impedance in accordance with the present invention, particularly direct measure of impedance, is that the measurement is generally independent of the shape of the probe and of whether the apparatus is operated in the torsional, axial or flexural mode. Moreover, the transducer can either be pulse driven, continuous wave driven or burst driven.

Crystal transducers have heretofore been widely used to convert alternating electrical energy into vibratory mechanical energy. Moreover, it is known to use multiple drive crystals in particular configurations to get the best results at harmonic frequencies. The present invention, however, incorporates a crystal sensor integral with the transducer to provide direct measurement of impedance.

The prior art method of measuring changes in physical characteristics of a material as a function of changes in impedance relies upon the measurement of the standing wave ratio. This requires two crystal detectors located at specific locations $\frac{1}{4}$ wave length apart; i.e., at the node and anti-node in a resonant system. It also requires that the probe be designed to be resonant; that is an integral number of $\frac{1}{2}$ wave lengths in length. Stated otherwise, in prior art systems the ultrasonic parameters tend to define the shape of the probe; i.e., length and shape of cross-section to obtain the requisite standing wave. In the present invention the probe can be shaped to be most suitable to the physical characteristic being measured. For example, where fluid flow is an important consideration, the probe can be configured so that a fluid properly flows around it. Still further, the crystal sensor or sensors for detecting impedance can be anywhere in the mechanical train of the transducer as long as it is mechanically in series with the drive crystals. This is true even though the preferred structure places the drive and sensing crystals in contiguous relationship.

Another disadvantage of the prior art is that in many instances the geometry of the probe changes due to corrosion, material build-up or other forms of damage. Such systems are also affected by changes in temperature, changes in the natural frequency of the crystal, and drift in the power. The probe is no longer in resonance. When this occurs the position of the node and anti-node shifts and their mathematical relationship loses meaning because the crystals are no longer separated by a $\frac{1}{4}$ wave length. Because the sensing crystal used in the present invention is not used to measure standing wave ratio, it can be placed anywhere in the mechanical train it is not affected by changes in the geometry of the probe or changes in other sensing characteristics.

Another advantage of the present invention is that the apparatus can be operated in continuous wave (CW), tone burst, or pulsed modes, whichever is most desirable for measuring a particular physical characteristic. Standing wave impedance measuring ultrasonic systems are limited to continuous wave modes of operation and thus are not as versatile. The present system can use the same transducer for any mode of operation.

The advantages of the present invention in measuring the characteristics of materials as a function of ultrasonic impedance are obtained by integrating the crystal sensor into the transducer and then measuring the decay in signal amplitude which is directly related to changes in impedance caused by changes in a character of the material. Such changes are measured by a servo-control system that is operable in any one of three modes.

For the purpose of illustrating the invention, there is shown in the drawings a form which is presently preferred; it being understood, however, that this invention is not limited to the precise arrangements and instrumentalities shown.

FIG. 4 is an operating cycle diagram.

Figure 1:
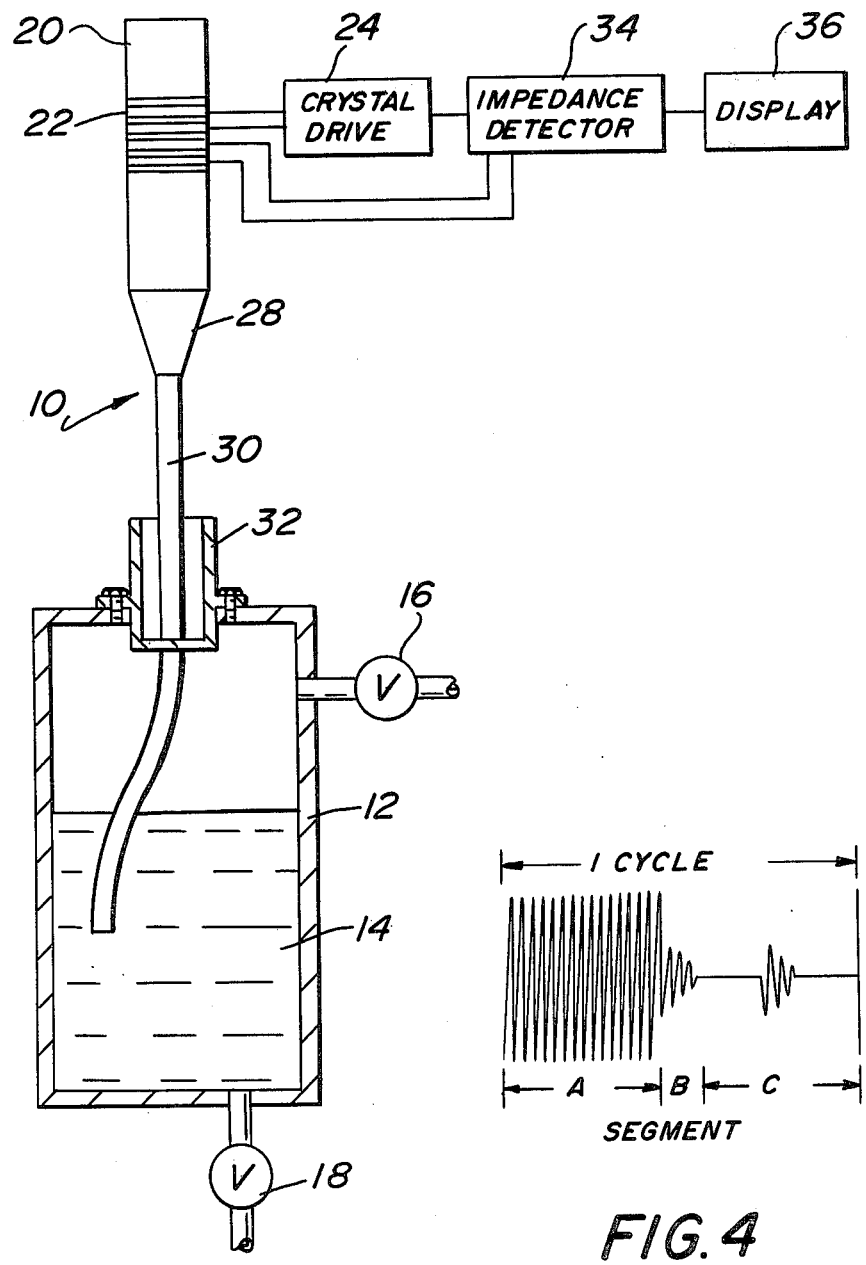
FIG. 1 is an elevational view of the apparatus, partially in section.

Referring to the drawings in detail, wherein like numerals indicate like elements, there is shown in FIG. 1 an ultrasonic apparatus designated in general by the numeral 10 for measurement of the characteristics of a material by measuring reflected ultrasonic impedance. The apparatus 10 is used as a level gage in the exemplary embodiment, the ultrasonic apparatus 10 as shown is shown mounted on a vessel 12 for containing fluid material 14 in variable quantities by admitting it through the valve 16 and withdrawing it through the valve 18.

The level of the liquid within the vessel 12 is determined by the apparatus 10. Such apparatus comprises transducer 20 which is described in more detail below. The transducer 20 is properly dimensioned to provide axial motion at the frequency of alternating electrical current applied to it through the drive crystals within the set of crystals 22. The drive crystals are energized by a source 24 of high frequency alternating current. Source 24 may comprise a stable oscillator and amplifier such as is known in the ultrasonic art. Typically, the frequency range of the source 24 is from 10 KHz to approximately 3 MHz although the preferred range may typically be between 15 KHz to 200 KHz. The particular frequency will depend upon the configuration of the transducer 20 and density of the material in same instances.

Transducer 20 is mounted upon acoustical coupling member 28 which is connected to probe 30. Member 28 and probe 30 are designed in accordance with known principles of ultrasonic energy to function as acoustic transmission lines for transmitting such energy into the vessel 12. Member 28 is a shaped acoustical coupling member defining a mechanical transformer for regulating the amplitude of the mechanical vibratory energy transferred into the probe 30. Probe 30 is of indefinite length and is designed in accordance with the anticipated range of levels of the liquid 14, consistent with known ultrasonic principles. Probe 30 may be curved or angled in whole or in part so that the axis of the probe is not constant in direction as shown in FIG. 1. Transducer 20, coupler 28 and probe 30 are designed in the illustrated embodiment to vibrate in the axial or longitudinal mode. The apparatus 10 is supported on the vessel 12 by the force-insensitive mount 32. Such force-insensitive mount may be of the type which is described in U.S. Pat. No. 2,891,180 entitled "Support for Vibratory Devices" and issued in the name of William C. Elmore.

If desired, the apparatus 10 could be directly fixed to the vessel 12 without a force insensitive mount. This may be useful where a limited amount of space is available.

Connected to the transducer 20 is an impedance measuring circuit 34. The impedance measuring circuit is connected to a pair of sensor crystals within the transducer 20 as explained below. Connected to the impedance circuit 34 is a display 36 for providing a readout of the impedance.

Figure 2:
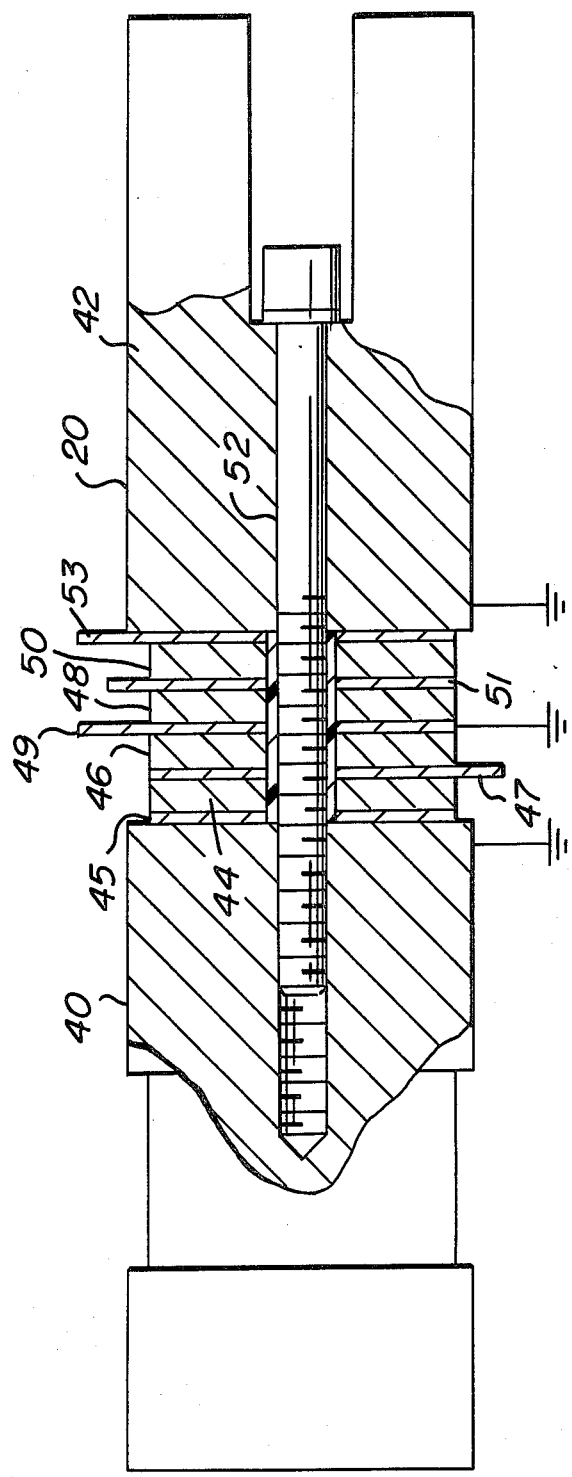
FIG. 2 is a transverse sectional view illustrating the integral crystal transducer.

Referring to FIG. 2, there is shown a transverse sectional view of the transducer 20. Transducer 20 comprises two ¼ wave end bells 40 and 42 with two pairs of crystals 44, 46 and 48, 50 and held in compression by the center bolt 52. As is known, the face of each crystal is coated with a conductor such as silver and is separated from adjoining crystal by the copper plates 45, 47, 49 and 51 which also function as electrical terminals. The crystals and plates are insulated from bolt 52 by sleeve 53. Bolt 52 is adjusted to apply sufficient force to the crystals so that they operate in the linear region of their operating curves.

Crystals 44 and 46 are connected electrically as sensor crystals and crystals 48 and 50 are connected electrically as transmitting or drive crystals for transducing electrical energy into mechanical energy. Crystals 48 and 50 generate the ultrasonic mechanical output signal of the transducer 20 to be used for sensing a characteristic of a material such as, by way of example, its level as a function of reflected acoustic impedance. The sensor crystals 44 and 46 detect a reflected acoustic signal and transduce it into an electrical signal which measures the change in characteristic of the material as a function of change in impedance. The circuitry for accomplishing this is illustrated in FIG. 3.

Although the sensor crystals 44, 46 are shown as contiguous with the drive crystals 48, 50, they could be located anywhere in the mechanical train of the apparatus as long as they are mechanically in series with the drive crystals 48, 50. However, for electrical and instrumentation convenience, the two drive crystals and two sensor crystals are 44, 46 contiguous, and they are placed in the center of a half wave system. Indeed, the only operational parameter that bears upon where the two crystal sets should be located is the inherent signal lag that the physical separation is equivalent to in the servo system.

It should be noted that although a pair of sensor crystals 44, 46 are used, a single crystal could also be used. The advantage of using a pair of crystals is to provide a bi-polar output into the servo circuit. With a single crystal the output could be in one direction only. In other words, the charge output would vary in amplitude but not direction. Thus, the use of a pair of crystals simplifies the electrical design. It should be noted, however, that by proper electrical design it is possible to use any integral number of sensor crystals. When using an odd number of crystals the electrical design must provide for isolation of each side of the crystal and provide the crystal signal to a differential input configuration amplifier. For electrical simplicity and signal quality, pairs of crystals are preferred because they can be operated with an electrical ground references terminal as shown.

Figure 3:
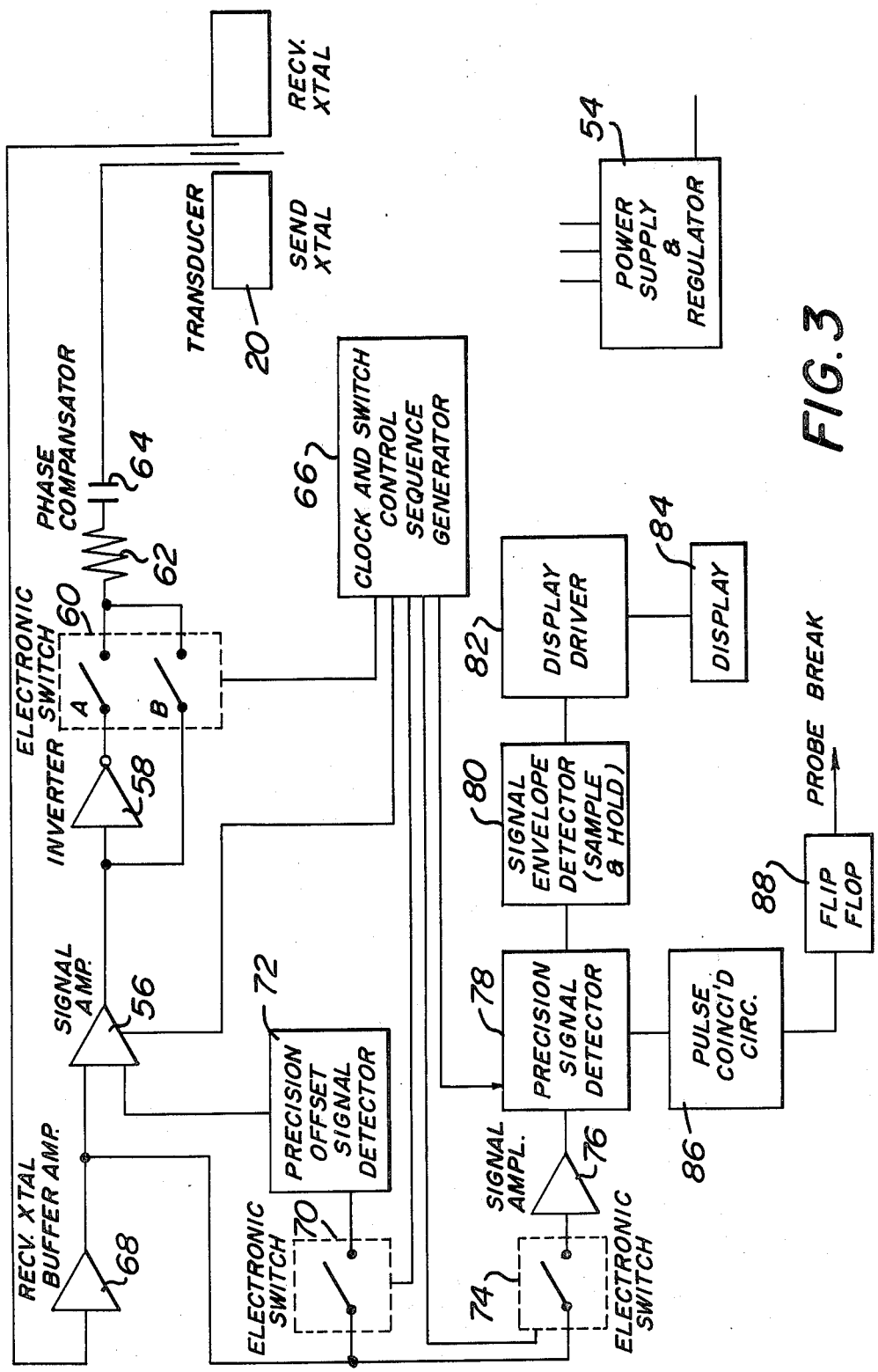
FIG. 3 is a block diagram of the electronic servo-control system.

In FIG. 3 there is shown a block diagram of a servo control circuit for operation of the apparatus.

FIG. 3 is a block diagram of the electronic control for the transducer 20. More particularly, it functions as a servo-control for determining changes in impedance to the ultrasonic acoustic energy delivered to the probe 30. The electronic control circuit can function in any one of three modes (continuous wave, burst, or pulse) as explained below.

Within the burst or pulse mode of operation, the electronic control circuit timing establishes repetitive operating cycles as illustrated in FIG. 4. Within a single cycle, the following segments, later described, occur:

(a) Regenerative segment of defined, controlled length of time where the transducer drive of the probe is generated at the appropriate transducer/probe operating frequency (20 KHz for example).

(b) Degenerative segment of defined, controlled length of time where the transducer oscillation is terminated in a rapid controlled manner.

(c) Sensing segment where reflected energy from the probe is detected and the signal processed.

The operation of the system may be at any cycle repetition rate that is convenient, however, for the present embodiment, rates between 10 and 500 operational cycles per second are envisioned with each cycle containing a defined number of transducer physical vibrations determined by the transducer operating frequency.

The drive crystals 48, 50 are electrically connected to the output of signal amplifier 56 through electronic switch 60 and the resistor-capacitor phase compensator 62, 64. Electronic switch 60 selectively connects the drive crystals to the signal amplifier 56 either directly through switch 60b or through inverting amplifier 58 and switch 60A. Control of the electronic switch 60 and all other electronic switches described herein is provided by the clock and switch control sequence generator 66 which is connected to each of the switches as shown. Clock and switch control sequence generator 66 open and closes the switches in proper sequence as described hereinafter.

Clock and switch control sequence generator 66 also provides the ultrasonic signal which is amplified by signal amplifier 56 and applied as a square wave to transducer 20.

To complete the closed servo loops, sensor crystals 44, 46 are connected through buffer amplifier 68 the non-inverting input of signal amplifier 56. The output of buffer amplifier 68 is connected through electronic switch 70 to offset signal detector 72. The offset signal detector 72 is connected to the inverting input of signal amplifier 56, and serves to augment the operation in the ringdown (degenerative) portion of the operating cycle.

The output of buffer amplifier 68 is also connected through electronic switch 74 to signal amplifier 76. The output of signal amplifier 76 is connected to signal detector 78 which is connected to envelope detector 80. Signal detector 78 is also connected to pulse coincidence circuit 86 which is connected to flip/flop circuit 88. Envelope detector 80 includes a sample and hold circuit as well as a comparison circuit. Its output is amplified in display driver 82 and displayed in display 84 in either analog or digital form.

The regulated power supply 54 provides power to each of the circuits. As is conventional and for simplicity, the electrical connection to each circuit is not shown.

The burst or pulse mode of operation is first explained. Both of these modes are essentially the same since the basic difference between the two modes is the length of time during which drive excitation is applied to the transducer. A pulse exists for a minimal amount of time, usually that time equivalent to a ½ wave whereas the burst of ultrasonic energy lasts for an integral number of waves of the transducer drive oscillation.

Initially, switch 60A is closed and switches 60B, 70 and 74 are open. This means that the servo loop is in a regenerative mode; that is the signal fed from the sensor transducers is 180° out of phase with the drive signal. Stated otherwise, the transducer 20 and associated electronics are configured as an oscillator, and by proper tuning, it is made to oscillate at the resonant frequency of the transducer 20. For the purposes of this discussion, it is assumed that the circuit has been tuned to the resonant frequency of the transducer 20 and any start up transients have been eliminated.

Switch 60A is closed and then opened after an appropriately defined amount of time, depending upon whether the apparatus is to be operated in the burst or pulse mode. As a result, an ultrasonic signal is generated by the transducer and transmitted into the material 14 or other material under test.

Then switch 60A is opened and switch 60B closed. Switch 70 is simultaneously closed. Consequently, the signal fed back from the sensor transducers connected through offset signal detector 72 to the inverting input of signal amplifier 56. Amplifier 56 now operates on the difference between the two signals at its input. The servo loop now operates in a degenerative mode. In other words, the output of the transducer is forced to decay.

Since, it is desirable that the ultrasonic signal be made to decay more rapidly than it would naturally self-damp so that the circuit can more quickly be made available for detection of the signal reflected back into the transducer. The offset signal detector 72 processes the signal fed back from the sensor transducers so as to augment the decay or ring down of transducer 20 thereby causing this to occur while the pulse or burst energy is still in the material 14. Offset signal detector shifts the zero base line of a portion of the sensing crystal signal resulting in a signal that augments the input to signal amplifier 56 in such a way that the transducer decays or rings down much more rapidly than would normally be experienced.

Switch 74 is also closed when switch 70 is closed. The resulting signal applied to signal detector 78 is a signal envelope which corresponds to the degree of oscillation of the transducer 20 as it decays. This signal envelope is a direct measure of the amount of input energy into the material. Signal envelope detector 80 integrates the wave envelope and stores that value in the sample-and-hold circuit.

At this time, electronic switch 60b is opened as is switch 70. As indicated above, the transducer 20 has been quieted, although it should be noted that a complete quieting is not achieved nor is it necessary. The ultrasonic energy retained within the probe 30 is reflected back into the transducer 20 and sensed by the sensor crystal 44, 46. The resultant electrical signal is transmitted through buffer amplifier 68, switch 74, signal amplifier 78 and signal detector to envelope detector 80 where it is integrated and may be displayed or compared to fixed reference voltages equivalent to fixed increments of probe immersion and the result of the comparison displayed (with or without making a permanent chart record) as an indication of the level of material surrounding probe 30 when properly calculated.

The signal is also passed to pulse coincidence circuit 86. If probe 30 is broken, there will be a change in time in which the reflected signal is received. This change in time is detected in the pulse coincidence circuit and causes a change of state in flip/flop 88 thereby energizing an alarm.

The circuit can be operated in the continuous wave mode. In this mode, switch 60 is never fully opened. The circuit merely measures changes in applied energy.

The system has been described as a level gage. However, a similar functional mechanization may be made for measuring changes in density in the material 14.

It should also be noted that although probe 30 is illustrated as a cylindrical rod, it could assume other shapes as determined by the type of material being evaluated. Moreover, the crystals could be designed to generate acoustical mechanical energy in a mode other than a longitudinal mode.

The present invention may be embodied in other specific forms without departing from the spirit or essential attributes thereof and, accordingly, reference should be made to the appended claims, rather than to the foregoing specification, as indicating the scope of the invention.

We claim:

1. Ultrasonic apparatus for measuring the characteristics of a material by sensing impedance to the ultrasonic energy driving a probe, comprising:
    a transducer including means whose electrical output varies with dimensional changes and whose dimensions vary with an applied electrical signal;
    said transducer being acoustically connected to a probe, said probe being adapted for insertion into a material whose characteristics are to be measured;
    means for sensing the ultrasonic acoustic energy in said probe and determining the equivalent impedance;
    said sensing means being in series mechanically with said transducer and including a closed loop servo control drive and means for operating said drive in the continuous wave, burst or pulse mode.

2. Ultrasonic apparatus in accordance with claim 1 including means for sensing loss of function of said probe.

3. Ultrasonic apparatus in accordance with claim 1, wherein the axis of said probe is not constant in direction.

4. A method of measuring the characteristics of a material by sensing impedance to the ultrasonic energy driving a probe, comprising the steps of:
    generating ultrasonic energy by using a transducer;
    delivering said ultrasonic energy through a probe into the material whose characteristic is to be sensed;
    sensing at the transducer the ultrasonic energy in the probe using a crystal detector that is integral with said transducer, and;
    determining the impedance equivalent of the ultrasonic energy sensed, and said ultrasonic energy being generated in one of the following modes: a continuation wave mode, a pulse mode, and a burst mode.

5. A method in accordance with claim 4 wherein said determining step includes measuring reflected ultrasonic impedance as a function of changes in transducer response to applied drive excitation.

6. Ultrasonic apparatus for measuring the characteristics of a material by sensing changes in impedance to the ultrasonic energy driving a probe, comprising:
    a transducer, including crystal means for generating ultrasonic energy and integral crystal means mounted coaxial with and mechanically in series with said first mentioned crystal means for sensing ultrasonic energy in said probe;
    an acoustic coupling member;
    said transducer being acoustically mounted on said acoustic coupling member;
    a probe, said probe being mounted to said acoustic coupling member for insertion into a material whose characteristics are to be measured;
    a means for sensing changes in the impedance to the ultrasonic acoustic energy delivered by said probe into a material.

7. Ultrasonic apparatus in accordance with claim 6 including a servo control circuit for excitation of the transducer and for sensing energy received by the transducer.

8. Ultrasonic apparatus in accordance with claim 7 wherein said servo control system includes means for shortening the time it takes for the transducer to decay from its resonant state to a quiesence state.

9. Ultrasonic apparatus in accordance with claim 6, including at least one force-insensitive mount attached to said probe for minimizing loss of energy to a support structure.

10. Ultrasonic apparatus in accordance with claim 6 wherein means is provided to automatically vary the operating frequency to maintain a resonance condition independent of physical or electrical parameter variations.

* * * * *